United States Patent [19]

Scalese

[11] 4,425,545

[45] Jan. 10, 1984

[54] EDDY CURRENT PROBE CALIBRATION STANDARD

[76] Inventor: Joseph J. Scalese, 5531 Laird Rd., Loomis, Calif. 95650

[21] Appl. No.: 286,816

[22] Filed: Jul. 27, 1981

[51] Int. Cl.³ .............................................. G01R 35/00
[52] U.S. Cl. .................................... 324/202; 33/178 B
[58] Field of Search ......................... 324/202; 73/1 R; 33/178 B, 168 R

[56] References Cited

U.S. PATENT DOCUMENTS 2,896,333  7/1959  Kivela ............................... 33/178 B
3,718,855  2/1973  Rogel et al. .......................... 324/202

FOREIGN PATENT DOCUMENTS 2837746  8/1978  Fed. Rep. of Germany ...... 324/202

*Primary Examiner*—Gerard R. Strecker
*Assistant Examiner*—Warren S. Edmonds
*Attorney, Agent, or Firm*—Donald J. Singer; William Stepanishen

[57] ABSTRACT

An eddy current probe calibration standard for calibrating eddy current probes and instruments utilizing calibration discs that provide a standard defect of known dimensions to produce a known repeatable signal. A plurality of round discs with different diameter holes through their centers are respectively provided to accommodate different size probes. Each disc has a defect in the wall of the hole in the form of a slot with known dimensions which will reproduce a known, repeatable signal. A flat, rectangular block which supports the discs, contains surface slots of known dimensions to produce known, repeatable signals for calibration when testing for surface defects.

8 Claims, 5 Drawing Figures

EDDY CURRENT PROBE CALIBRATION STANDARD

STATEMENT OF GOVERNMENT INTEREST

The invention described herein may be manufactured and used by or for the Government for governmental purposes without the payment of any royalty thereon.

BACKGROUND OF THE INVENTION

The present invention relates broadly to eddy current probes and instrumentation, and in particular to an eddy current probe calibration standard.

In the prior art, various methods to detect fatigue cracks in fastener holes and other critical areas of aircraft structural parts have become routine inspection requirements. Depending upon the acceptance limits established for inspection of hole cracks in a wing fitting for example, nondestructive test methods, techniques, and procedures are developed. X-rays are useful when gross cracks can be tolerated, or if accessibility is a problem. Ultrasonics can be used to detect cracks smaller than those found by x-rays, and when fasteners cannot be removed. Penetrants will detect cracks that are open to the surface, but are often times limited in their usefulness due to any foreign material embedded in a cracked area. Optical methods are extremely useful for showing small flaws, but extensive hole preparation is necessary in order to clean foreign materials and smeared metal from the hole surface. The methods for magnetic rubber and magnetic particle inspection of ferromagnetic parts have been developed utilizing soft iron indicators and electronic instruments to measure magnetic fields. While these methods are very desirable for inspection of steel parts, they are time consuming and require extensive surface preparation. Eddy currents inspection methods using both surface, and bolt hole probes, can detect not only small cracks, but requires a minimum of surface preparation. Because of these advantages, eddy currents are often selected as the primary inspection method.

Eddy Current inspection techniques for nondestructive testing of fasteners holes and surface areas such as aircraft wing skins, and other structural parts requires that flaw information be obtained from probe contact to the material under test. Eddy current testing is based on the conductivity of the material which is primarily determined by the material's chemical composition. When a test coil is placed above the surface of an isolated conducting material, the coil's magnetic field induces current into the material. The eddy current field developed by the flow of eddy currents will vary as the flow of eddy currents varies. Cracks inclusions, and changes in conductivity will cause this flow to vary. This is accomplished by a hand held probe, or by using an automatic scanner which rotates the eddy current probe continuously 360° throughout the length of a fastener hole undergoing inspection. This automatic system makes use of the same general principles as mentioned above and has been established by hand-scan methods.

The primary requirement for an eddy current calibration standard is to provide a valid calibration of probe and instrument for a response which can be related to the minimum crack size to be detected. This requirement was not being satisfied prior to the invention since a basic calibration standard had not been established for general use by private industry, the Air Force, or other governmental agencies. Many nondestructive test personnel in the field do not have facilities to manufacture reference blocks such as the present block with a single saw cut edge.

For many years, nondestructive inspection personnel have tried to determine an eddy current probe's sensitivity from a small (45°) forty-five degree jewelers saw cut made at the edge of a hole for a specific size probe. A signal is transmitted from the probe and a crack-like indication is obtained from an eddy current instrument, and a trace made with a high speed recorder. This simulated defect, at best, serves only as a metal flaw reference. However, it could not be related to any specific defect or crack size. Further, this has never provided a valid, repeatable, traceable method of eddy current probe and instrument calibration.

SUMMARY OF THE INVENTION

The present invention utilizes a precision manufactured disc to fit various size probes for calibrating eddy current probes and instruments by using a set of test defects having known dimensions and characteristics. In the calibration of a probe to be used in the inspection of bolt holes or other fastener holes, for example, a plurality of round discs are used having different diameter holes through their centers to accommodate different size probes. Each size calibration disc has a defect in the wall of the hole in the form of a slot of known dimensions which will reproduce a known, repeatable signal. A flat, rectangular block for supporting, for example, three discs, is provided with surface slots of known dimensions to produce known, repeatable signals for calibration when testing for surface defects.

In order to provide optimum sensitivity and reliability for crack detection, calibration of eddy current probes and measuring systems with a repeatable, traceable standard is of paramount importance. Variables critical to an instrument's performance must be checked to a known value.

It is one object of the present invention, therefore, to provide a new valid eddy current probe calibration standard.

It is another object of the invention to provide an improved eddy current calibration probe standard to accommodate a wide range of calibration holes for various size probes.

It is another object of the invention that new and used probes can be evaluated for sensitivity capabilities prior to being used on an inspection task.

It is still another object of the invention to provide an improved eddy current probe calibration standard wherein the calibration standard produces a true material signal by means of a thru slot since the edge effect is eliminated.

It is yet another object of the invention to standardize the calibration of eddy current probes along with measuring systems now in use.

It is yet another object of the invention to provide an improved eddy current probe calibration standard wherein a recorder amplitude may be set for inspection levels of acceptance or rejection.

It is another object that the invention be especially valuable for flaw detection in the lower crack size ranges. The thru slot provides an accurate instrument setting for determining crack sizes from 0.010 to 0.045 inch with the use of shielded probes.

It is still a further object of the invention to provide an improved eddy current probe calibration standard which is economical to produce and utilizes conventional, currently available components that lend themselves to standard mass production manufacturing techniques.

These and other advantages, features and objects of the invention will become more apparent from the following description taken in connection with the illustrative embodiment in the accompanying drawings.

DESCRIPTION OF THE PREFERRED EMBODIMENT

Figure 1:
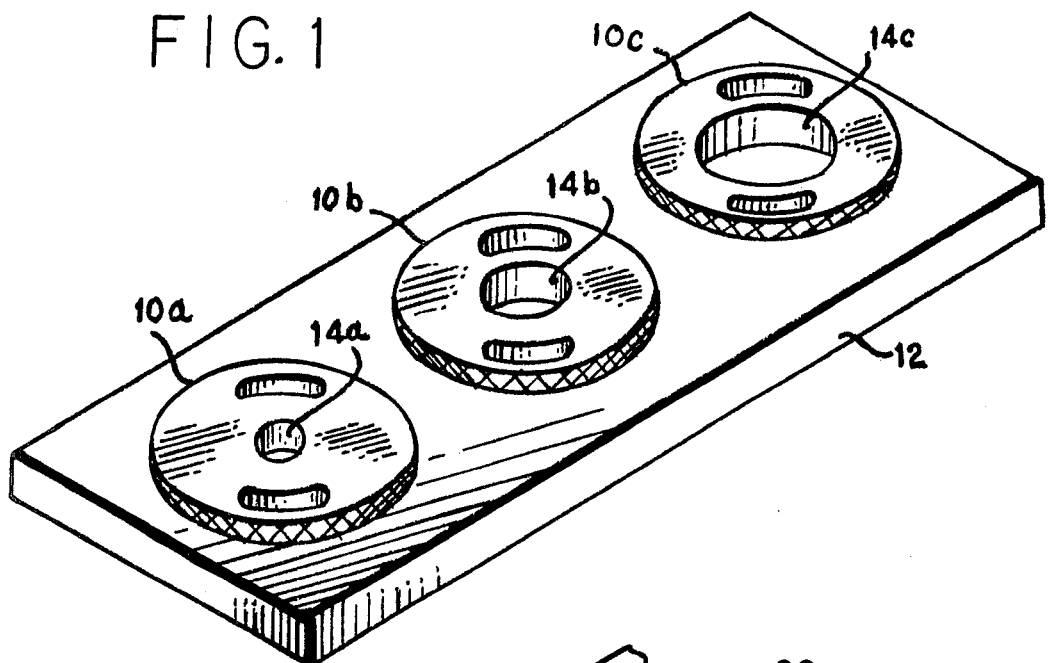
FIG. 1 is a perspective view of the eddy current probe calibration standard according to the present invention.

Referring now to FIG. 1, there is shown an eddy current probe calibration standard with three replaceable calibration discs 10a–c positioned in a holding block fixture 12. The calibration discs 10a–c are circular metal discs with different size holes 14a–c precision machined through the centers thereof. The calibration discs 10a–c are comprised of a suitable material to conduct eddy currents. The holes 14a–c are provided in the calibration discs 10a–c to permit the insertion of an eddy current probe into its corresponding calibration disc wherein a calibration slot or flaw is provided. The details of the calibration slot in each of the calibration discs 10a–c will be shown and described in greater detail in FIG. 2. The holding block fixture 12 is comprised of a suitable metallic material and in the present example is 5¼ inches in length, 2½ inches in width and ¼ inch in thickness. All dimensions herein are given in inches.

Figure 2:
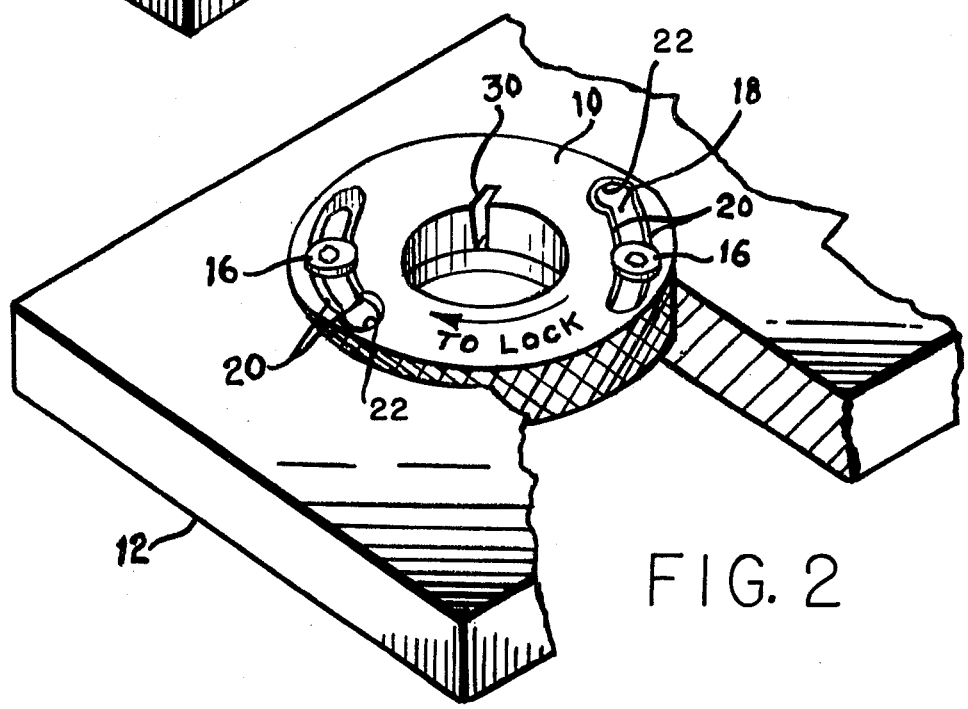
FIG. 2 is an isometric view, partly in section, of a calibration disc positioned in the holding block fixture.

Turning now to FIG. 2, there is shown a sectional view of the holding block fixture 12 a calibration disc 10 that is removably mounted therein. The calibration disc 10 may be attached to the holding block fixture 12 in any convenient conventional manner or as shown wherein a tapered elongated slot and bolt are utilized. The retaining bolt in the present example is shown as a cap screw 16 which is threaded into the holding block fixture 12. The tapered slot 18 has a shoulder 20 on either side of the slot to provide a mating surface for the retaining bolt 16. One end of each tapered slot 18 has an enlargement 22 therein (this detail is better shown in FIG. 3) to permit the retaining bolt 16 to pass freely through the calibration disc slot when either installing or removing the calibration disc 10. During the removal of the calibration disc 10, the retaining bolts 16 may be loosened but not removed to facilitate removal of the calibration disc 10. During an eddy current probe calibration procedure, the retaining bolts 16 may be securely fastened to maintain the calibration disc in a fixed position during the calibration period.

Figure 3:
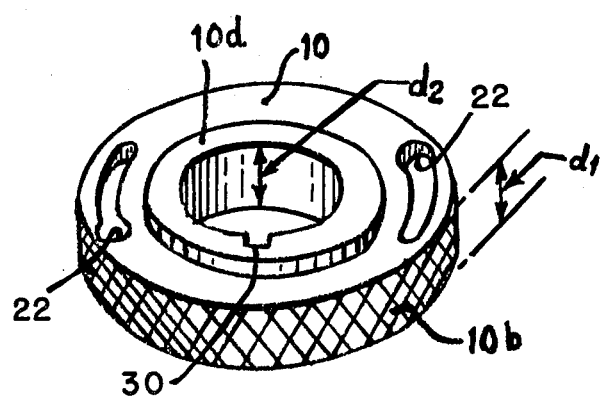
FIG. 3 is a bottom view of a calibration disc.

The calibration disc 10 has a precision machined calibration thru slot 30 positioned in the wall of the hole of the calibration disc. The calibration slot 30 is substantially perpendicular to the top and bottom surfaces of the calibration disc 10. The calibration slot 30 is a machined or otherwise constructed slot of a predetermined known dimension that will produce a reproducible, known, true signal. As shown in FIGS. 2 and 3, the calibration slot 30 extends along the entire surface of the hole wall in the calibration disc 10 from the top surface to the bottom surface. In the present example, the calibration slot 30 has a slot depth of 15 to 20 thousandths and a width of 5 to 8 thousandths. All slot dimensions are measured in inches. It will be well understood that the particular dimension of the slot which is required for a particular application may be varied to satisfy the test standard criteria. Thus, it may be seen that slot depth may be varied between 10 to 40 thousandths for surface probe calibration.

In FIG. 3, there is shown a bottom view of the calibration disc 10 in order to provide a greater detail view of the lower surface of the calibration disc. The calibration disc 10 has an overall outside diameter or $OD_1$, of 1.400 inches, plus or minus 0.020 inches. A raised circular portion 10a is provided in the bottom of the calibration disc 10 to provide a secure seating surface for the calibration disc in the holding block fixture. The raised circular portion 10d has an outside diameter, $OD_2$ of 0.875 inches plus or minus 0.001 inches. The outer surface 10b of the calibration disc 10 is knurled to provide to faciliate handling while turning the calibration disc in the holding block fixture when either locking or unlocking the disc therein. The calibration disc 10 has an outer edge thickness, $d_1$ of 0.187 inches and in the hole portion of the disc, has a thickness, $d_2$ of 0.250 inches. The difference between the two dimensions, $d_2 - d_1$ equals the height of the raised circular portion 10a with respect to the lower surface of the calibration disc 10. This difference, $d_2 - d_1$, equals 1/16 of an inch or 0.0625 inches.

Figure 4A:
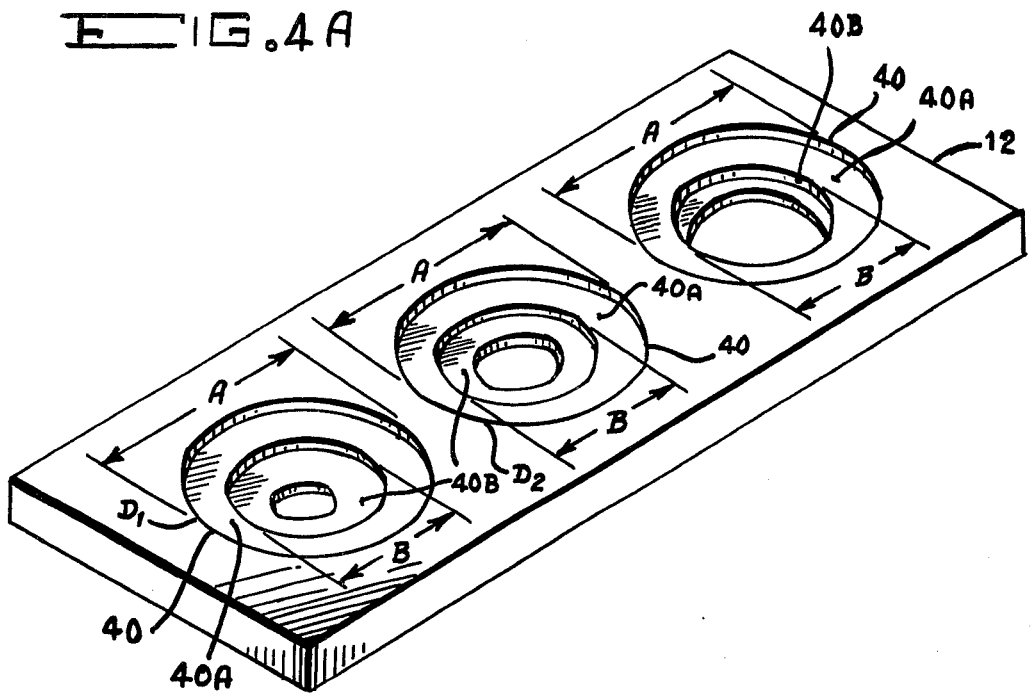
FIG. 4a is a top view of the holding block fixture.

Referring now to FIG. 4a, there is shown a top view of the holding fixture block 12 wherein the calibration disc seats are shown in greater detail. The calibration disc seats 40 comprise a stepped hole arrangement wherein the first stepped hole 40a has a diameter, A which is equal to the outside diameter $OD_1$ of the calibration disc which is 1.400 inches. The first stepped hole 40a has a depth, $D_1$ which is equal to 0.080 inches plus or minus 0.002 inches. The second stepped hole 40b has a diameter, B which is equal to the outside diameter, $OD_2$ of the raised circular portion of the calibration disc. The second stepped hole diameter, B is equal to 0.875 inches plus or minus 0.002 inches. The third hole in the stepped hole arrangement in the holding block fixture 12 corresponds to preselected eddy current probe diameters and the corresponding hole in the calibration disc.

Figure 4B:
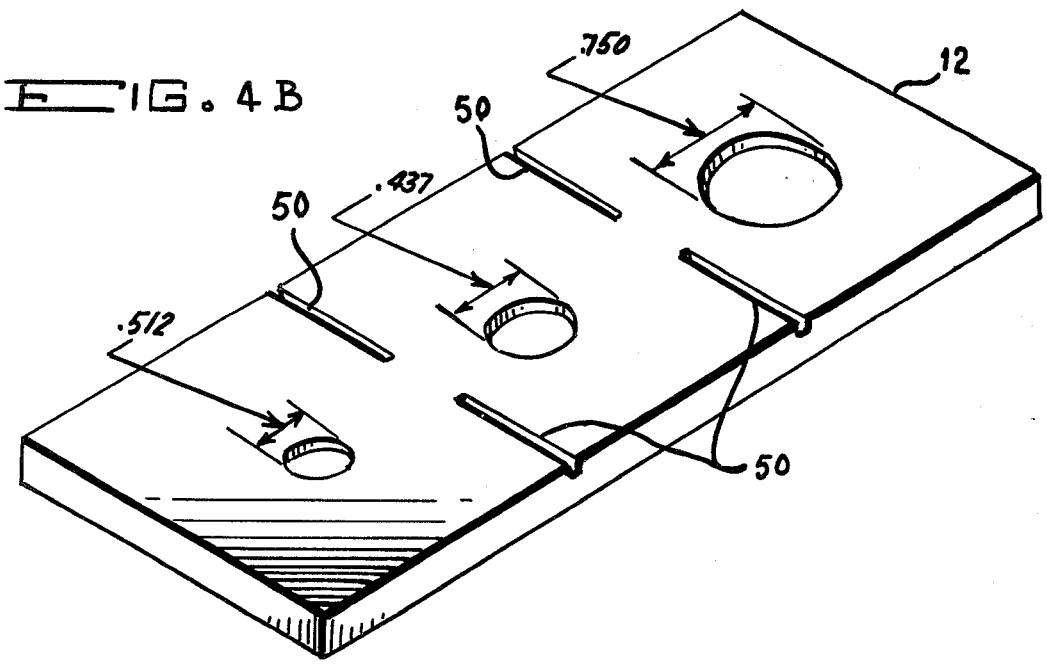
FIG. 4b is a bottom view of the holding block fixture.

In the present example, the diameter of the eddy current probe holes in the holding block fixture 12, as shown in the bottom view thereof in FIG. 4b, are respectively given as 0.512, 0.437 and 0.750 inches. These hole diameters correspond to the outside diameters of the eddy current probes that would be calibrated. It may be noted that this hole diameter may be varied according to the probe diameters which are currently in the range of ⅛ to 1½ inches. There is also shown on the bottom side of the holding block fixture 12, surface defects 50 which are cut into the bottom surface. The surface defects 50 may be utilized to calibrate a surface eddy current probe. The surface defects 50 comprise slots that are similar in dimension to the calibration slot 30 of FIG. 2 and are machined into the bottom surface of the holding block fixture 12. However, the dimensions of the surface defects 50 may be varied to cover any of a number surface eddy current probe test conditions.

The Calibration Standard is especially valuable for the calibration of the Automatic Eddy Current Flaw Detection System which is rapidly replacing the hand scanning technique for periodic inspection of fatigue cracks that develop on surfaces and in fastener holes of structural assemblies. Inspection results can be viewed with a high degree of confidence since a complete calibration of the automatic system is accomplished. Correlation of instrument sensitivity and recorder amplitude can be made to give a relative response from test standard to a minimum flow indication, while simultaneously proving the system.

Although the invention has been described with reference to a particular embodiment, it will be understood to those skilled in the art that the invention is capable of a variety of alternative embodiments within the spirit and scope of the appended claims.

What is claimed is:

1. An eddy current probe calibration standard for the calibration of an eddy current probe comprising in combination:
   a holding block fixture to provide a plurality of seating means,
   a plurality of calibration discs seated respectively in said plurality of seating means in said holding block fixture, said plurality of calibration discs comprising a suitable material to conduct eddy currents, each of said plurality of calibration discs having a central hole therein to accept an eddy current probe for calibration thereof, each of said holes being of different diameters, each of said holes containing a slot disposed in the wall of the hole, said slot having a longitudinal axis, said longitudinal axis of said slot being parallel to the central axis of said hole, said slot having predetermined dimensions, said slot providing a known defect to said eddy current probe for the adjustment thereof, and means for holding said calibration discs in said holding block fixture.

2. An eddy current probe calibration standard as described in claim 1 wherein each of said plurality of seating means comprises at least two holes, each of said holes having a plurality of steps therein, each of said steps defining a first diameter, second diameter and a third diameter respectively.

3. An eddy current probe calibration standard as described in claim 1 wherein said holes of different diameter will accommodate an eddy current probes of a corresponding diameter.

4. An eddy current probe calibration standard as described in claim 1 further including a plurality of predetermined surface defects in the surface of said holding block fixture.

5. An eddy current probe calibration standard as described in claim 2 wherein the first diameters are equal.

6. An eddy current probe calibration standard as described in claim 2 wherein said second diameters are equal.

7. An eddy current probe calibration standard as described in claim 2 wherein said third diameters are not equal.

8. An eddy current probe calibration standard as described in claim 4 wherein each of said plurality of predetermined surface defects define a slot of predetermined dimensions.

* * * * *